United States Patent [19]
Coulson

[11] Patent Number: 5,525,197
[45] Date of Patent: Jun. 11, 1996

[54] ELECTROCHEMICAL DETECTOR CELL, METHOD AND PYROLYSIS FURNACE

[76] Inventor: Dale M. Coulson, 21 Willow Rd., Apt. 13, Menlo Park, Calif. 94025

[21] Appl. No.: 302,665

[22] PCT Filed: Oct. 26, 1992

[86] PCT No.: PCT/US92/09057
§ 371 Date: Aug. 31, 1994
§ 102(e) Date: Aug. 31, 1994

[87] PCT Pub. No.: WO93/09426
PCT Pub. Date: May 13, 1993

[51] Int. Cl.$^6$ .................................................. G01N 27/26
[52] U.S. Cl. .................. 205/775; 205/780; 205/780.5; 205/779.5; 205/786.5; 204/416; 204/412; 204/411; 204/409; 422/98; 422/78; 422/80; 422/89; 422/82.02; 422/82.03; 422/82.04; 422/88; 422/90; 436/149; 436/150; 436/155; 219/390; 219/391
[58] Field of Search .................... 204/412, 405, 204/409, 435, 153.13, 153.23, 153.1, 153.19, 153.14; 436/149, 155, 161, 150; 422/76, 78, 80, 89, 98, 68.1, 82.02, 82.03, 82.04, 90, 88; 324/464, 468, 451; 219/390, 391; 126/343.5 R, 343.5 A, 226, 284

[56] References Cited

U.S. PATENT DOCUMENTS

| | | | |
|---|---|---|---|
| 3,741,728 | 6/1973 | Sistig et al. | 204/405 |
| 3,972,682 | 8/1976 | Stephens et al. | 219/390 |
| 4,440,726 | 4/1984 | Coulson | 204/405 |
| 4,786,372 | 11/1988 | Jones et al. | 204/409 |
| 5,017,339 | 5/1991 | Marsoner et al. | 204/409 |
| 5,019,517 | 5/1991 | Coulson | 422/89 |

*Primary Examiner*—Bruce F. Bell
*Attorney, Agent, or Firm*—Flehr, Hohbach, Test, Albritton & Herbert

[57] ABSTRACT

An electrochemical detection cell (320), which is usable either for potentiometric or electrolytic conductivity detection, has a capillary (305), which controls electrolyte flow. A gas stream containing detectable substances is input through a non-wettable plastic capillary (306). A reaction zone (310) through which both gas and liquid flow is internally wettable. Reference electrode (309) and either electrode (311) or (312) may be used for potentiometric detection. Sensor electrodes (311) and (312), both in the reaction zone, are used for conductivity detection. The electrolyte is fed through the capillary (305) gravimetrically from a reservoir, and the gas stream is supplied by a pyrolysis furnace. The mechanism of ionization in the gas phase ionization detector (GPELCD) is described.

32 Claims, 9 Drawing Sheets

FIG.—4

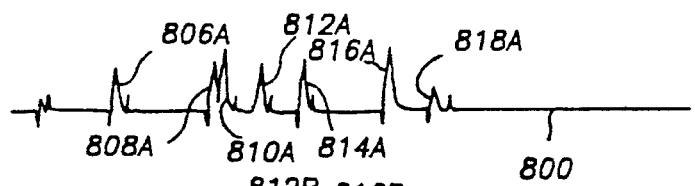
FIG.—10A
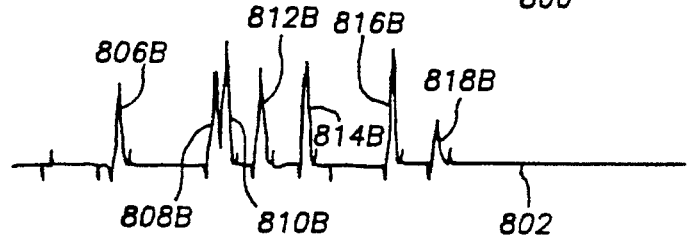
FIG.—10B
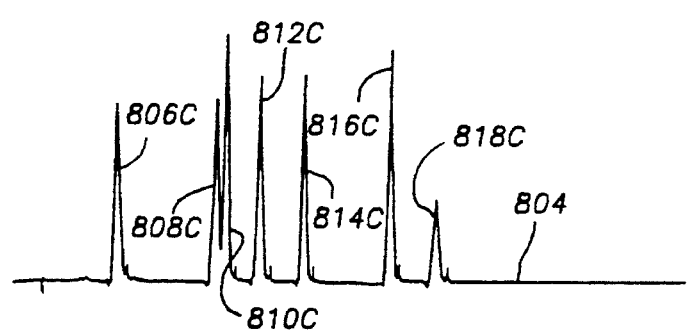
FIG.—10C
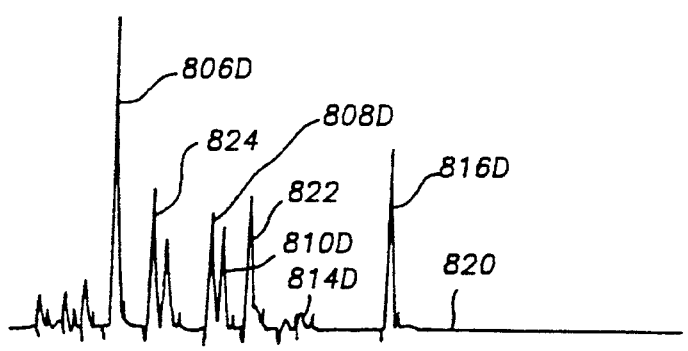
FIG.—10D

ELECTROCHEMICAL DETECTOR CELL, METHOD AND PYROLYSIS FURNACE

BACKGROUND OF THE INVENTION

1. Field of the Invention

The present invention relates generally to an improved electrochemical detector cell, an electrochemical detection method, and a pyrolysis furnace for use in electrochemical detection. More particularly, the invention relates to such a cell and method which is especially adapted for gravimetric flow. The invention further relates to such a cell and method that is usable for potentiometric, coulometric or conductimetric electrochemical detection.

2. Description of the Prior Art

Before 1950, it was common to determine the elemental composition of organic samples by combusting them and measuring the masses of simple compounds, such as carbon dioxide and water, produced. This method was called microcombustion analysis.

During the 1950s, gas chromatography (GC) was discovered, so there was a lot of research in the late 1950s and early 1960s on GC instrumentation, including sensitive detectors. Thermal conductivity detectors were soon followed by more sensitive and selective detectors, such as hydrogen flame ionization, electron capture, argon ionization, mass spectrometric and several electrochemical detectors. The first electrochemical detectors for use in chromatography were described in U.S. Pat. No. 3,032,493, issued May 1, 1962 to Coulson and Cavanagh. The use of the Coulson and Cavanagh detector with GC is described in Coulson et al., "Microcoulometric Gas Chromatography of Pesticides", Agricultural and Food Chemistry, 8, 399–402 (Sept:Oct. 1960) and Coulson, "Electroanalytical Instrumentation", ISA Fall Instrument-Automation Conference, Preprint No. 181-LA-61 (Sep. 11–15, 1961).

This detection system contained essentially all of the important features of the electrolytic conductivity detectors that were subsequently developed, including:

1) An effluent gas stream from a gas chromatograph.
2) A pyrolizer to convert organic compounds to simple substances, such as carbon dioxide, hydrogen chloride, ammonia and water.
3) A supply of liquid supporting electrolyte.
4) A contact zone to transfer electrolytes from the gas phase to the liquid phase.
5) Electrodes in contact with the liquid phase.
6) Means for measuring the electrolyte concentration in the liquid phase.

In microcoulometry, the means for measuring is based on potentiometry and titrant generation. In electrolytic conductivity, this means is simply measurement of the ohmic resistance between two electrodes.

U.S. Pat. No. 3,158,466, issued Nov. 24, 1964 to Sternberg was the first to report on the use of electrical conductivity in gas chromatography of halogenated organic compounds. The Sternberg system has all of the above elements for the microcoulometric detector. Sternberg did not disclose a structure for gas-liquid separation, but did suggest that electrolytes other than water may be used to achieve better sensitivity.

Almost simultaneously, Piringer, et at. reported the development of an electrolytic conductivity detector for GC in "Construction and Operation of the Electrolytic Conductivity Detector," J. Chromatog. 8, 410 (1962). They added an additional feature to the six listed above:

7) A gas-liquid separator for an electrolytic conductivity detector.

U.S. Pat. No. 3,309,845, issued Mar. 21, 1967 to Coulson, discloses an electrolytic conductivity detector utilizing a capillary in the gas-liquid contact zone of 1 to 0.1 mm inside diameter. With the 1 mm capillary, a liquid flow rate of approximately 1 ml. per minute was commonly used, with lower flow rates if the contact zone had a pumped liquid flow. This detector was provided in a commercial product by Tracor. Western Scientific Associates continues to market this detector under license from Tracor, but with the substitution of a modified pump flow controller.

U.S. Pat. No. 3,649,498, issued Mar. 14, 1972 to Pretorious et al. discloses a liquid and gas chromatographic detector cell in which a variety of solvents, including the lower alcohols, in addition to water are used as a carder liquid in the detector cell.

U.S. Pat. Nos. 3,934,193 and 4,032,296, issued Jan. 20, 1976 and Jun. 28, 1977 to Hall, repeat much of the above teaching and disclose unitized detector cells with structure for the physical separation of gas and liquid phases from samples being measured by the cells.

U.S. Pat. No. 4,440,726, issued Apr. 3, 1984 to Coulson discloses a reduced volume, all capillary detection cell suitable for potentiometric and coulometric detection cells. The present invention is a modification of that detection cell.

U.S. Pat. No. 5,019,517, issued May 28, 1991 to Coulson discloses a pyrolysis furnace which incorporates electrodes for detecting ion currents. There is a continuing need for improvement of pyrolysis furnaces, especially for supplying gases incorporating substances to electrochemical detection cells separate from the furnace.

SUMMARY OF THE INVENTION

Accordingly, it is an object of this invention to provide a detector cell configuration and detection method that are especially adapted to provide a controlled flow rate of solvent liquid through the cell.

It is a further object of the invention to provide such a detector cell and method in which the flow rate of the solvent liquid through the cell is controlled gravimetrically.

It is another object of the invention to provide such a detector cell and method that can be used for potentiometric, coulometric or conductimetric detection.

It is still another object of the invention to provide such a detector cell and method which is adapted to provide sensitivities in the picogram per second range.

It is yet another object of the invention to provide such a detector cell and method which provides a high degree of selectivity for elements to be detected.

It is a further object of the invention to provide an improved pyrolysis furnace especially configured for use with the detector cell.

The attainment of these and related objects may be achieved through use of the novel electrochemical detector cell, detection method and pyrolysis furnace herein disclosed. An electrochemical detector cell in accordance with this invention has an electrolyte input flow capillary tube intersecting a second capillary tube at a given point. A gas stream input flow capillary tube for a gas containing a substance to be detected enters the second capillary tube proximate to the given point. The second capillary tube forms a mixing zone at the given point. At least one sensor electrode is positioned in the second capillary tube spaced from and above the given point. The second capillary tube has an exit for the electrolyte and the gas stream beyond the at least one sensor electrode.

An electrochemical detection method in accordance with the invention includes supplying an electrolyte solution through an electrolyte input flow capillary tube to a mixing zone at a controlled flow rate. A gas containing a detectable substance is supplied through a gas input capillary tube to the mixing zone. The electrolyte solution and the gas are mixed in the mixing zone. The electrolyte solution and gas are passed from the mixing zone to a detection zone. The detectable substance in the electrolyte solution is detected within the detection zone. The detector zone may be very simple and not contain a gas-liquid separator or more complicated and have sensor electrode(s) in a gas-liquid separator as has been used in previously developed electrochemical detectors. The gas-liquid separator decreases the detector electrical noise and also tends to cause sharp peaks to broaden, called tailing. The electrolyte solution and gas are flowed from the detection zone.

A pyrolysis furnace for use with an electrochemical detection cell in accordance with this invention has first and second concentrically positioned electrically insulating tubes. A resistance heater is wound around said first electrically insulating tube between said first electrically insulating tube and said second electrically insulating tube.

The attainment of the foregoing and related objects, advantages and features of the invention should be more readily apparent to those skilled in the art, after review of the following more detailed description of the invention, taken together with the drawings, in which:

BRIEF DESCRIPTION OF THE DRAWINGS

FIGS. 9A and 9B and FIGS. 10A–10D are curves plotting experimental results obtained with the invention.

FIGS. 1–8 are in accordance with the invention.

DETAILED DESCRIPTION OF THE INVENTION

Figures 1, 2:
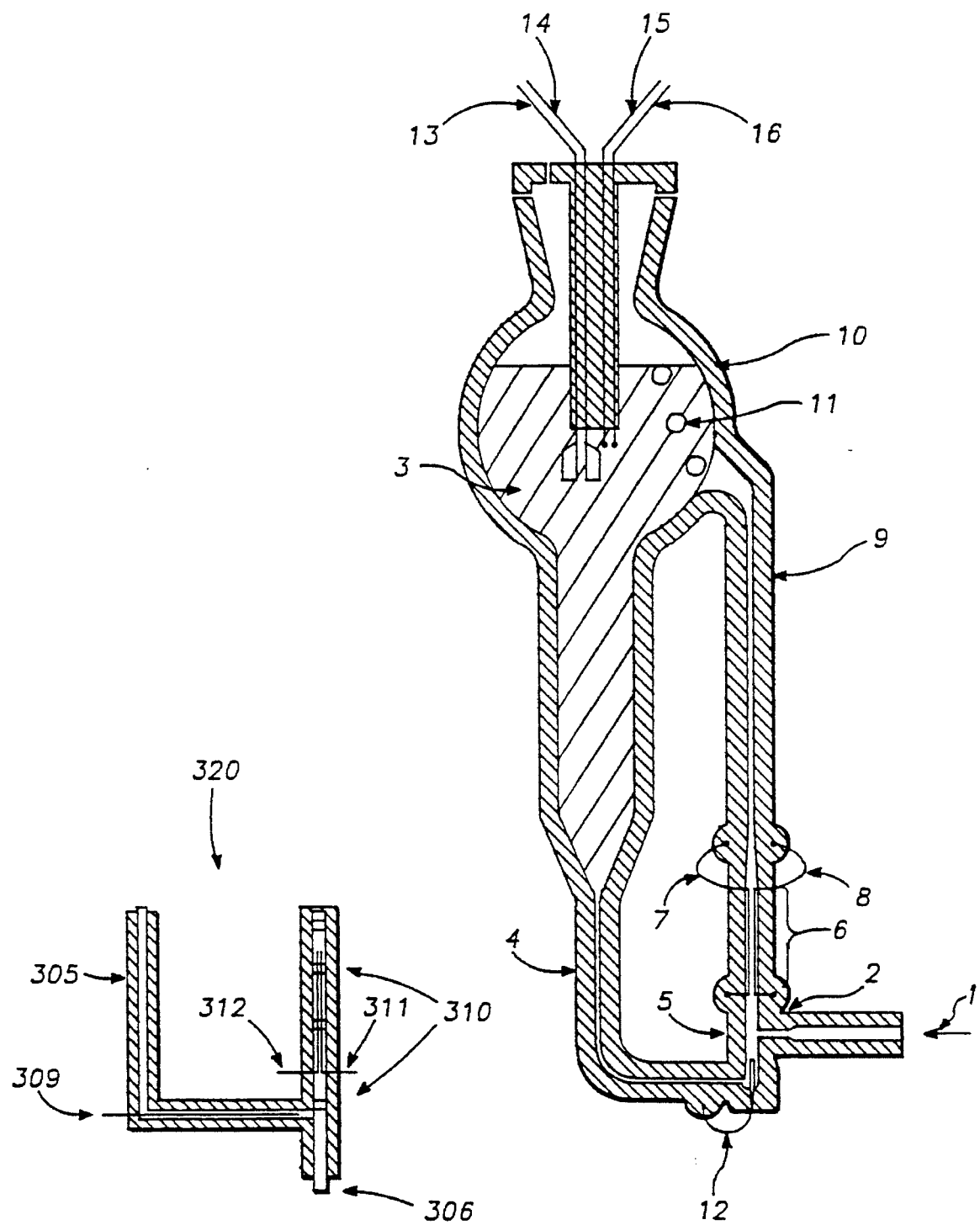
FIG. 1 is a cross section view of an electrochemical detection cell.
FIG. 2 is a cross section view of a potentiometric detector incorporating gravimetric solvent feed.

In connection with the present invention, the ionization mechanism of the detector described in my U.S. Pat. No. 5,019,517 has been elucidated. The ionization mechanism is as follows:

If the gas phase in the detector is primarily oxidative, most of the chlorine will be completely oxidized. The chlorine will thus be in the form Cl. and $Cl_2$. In this description, Cl. refers to all of the oxidized chlorine, such as $ClO$, $ClO_2$ and Cl.. The equilibrium constant for chlorine is in equation 1.

$$K' = (Cl.)^2/(Cl_2) \qquad (1)$$

Consequently, most of the chlorine is Cl. at low concentrations and $Cl_2$ at high concentrations. Since only the Cl. is detected, linear sensitivity is only available at low levels. At high levels of chlorine, the sensitivity is in proportion to the square root of $Cl_2$, since $(Cl.) = (K'*(Cl_2))^{0.5}$, and in between, the sensitivity gradually goes from linear to square root.

If reductive gases, such as hydrogen, are used in the detector, most of the chlorine is in the form of HCl. The amount of Cl. here is shown in Equation 2.

$$K'' = (Cl.)*(H_2)^{0.5}/(HCl) \qquad (2)$$

and with high concentrations of $H_2$, $K''$ simply becomes K as shown in Equation 3.

$$K = (Cl.)/(HCl); \text{ and } (Cl.) = K(HCl) \qquad (3)$$

Thus, the concentration of Cl. is nearly linear in terms of the total amount of chlorine in the gas phase that flows through the detector, since K is less than one tenth. At 700° to 1100° C., approximately 80 to almost 100% of the chlorine is in the form of HCl, thus the sensitivity is lower in the reductive condition than it is in the oxidative condition. Also, the reductive conditions yield $H_2S$ and $NH_3$, both of which yield smaller currents than chlorine. The sensitivity for N and S is on the order of one hundredth to one thousandth of the sensitivity for Cl, Thus, the reductive detector may also be used for other elements than Cl, such as N, S, and phosphorus.

If high sensitivity is desired, oxidative procedures may be used. If linear sensitivity at all Cl. concentrations is desired, reductive procedures may be used. Here the sensitivity is still in the order of 0.1 equivalent per mole of chlorine, while in oxidative conditions, the sensitivity may be as great as 2 or 3 equivalents per mole. Flame ionization detectors (FIDs) normally have a sensitivity of $10^{-4}$ equivalents per mole.

Chlorine detection is described above, and bromine is also detected similarly. This detector (a gas phase electrolytic conductivity detector, GPELCD) is selective for halogens and is insensitive to carbon, oxygen and hydrogen.

In the detector described in U.S. Pat. No. 5,019,517, the ionization of Cl. is catalyzed on metal electrodes in the presence of alumina, or other materials, such as mullite, but not limited to such materials. Such detection can be accomplished in any detector that has the proper gas phase and temperature. Thus a FID can be modified to give response to chlorine rather than carbon. In fact, a FID can have two phases; at the fast phase in the usual FID configuration, carbon is detected, and in the second phase, at a much higher temperature, chlorine and other halogens are selectively detected. In this case, chlorine is converted primarily to HCl using the ordinary gas composition used in the FID, which contains both hydrogen and oxygen that create $H_2O$. In the presence of water at these high temperatures, chlorine is primarily in the form of HCl. At nanogram levels of chlorine, linear detector responses are observed in the gas composition that is emitted from an ordinary FID.

Turning now to the drawings, more particularly to FIG. 1, there is shown an electrochemical detection cell 320, which is usable either for potentiometric or electrolytic conductivity detection. Capillary 305, composed of Pyrex glass, controls electrolyte flow and has an inside diameter of 0.1 to 1 mm. The gas stream containing the detectable substances is input through a non-wettable plastic, such as polytetrafluoroethylene, capillary 306. The reaction zone 310 through which both gas and liquid flow is internally wettable, such as Pyrex glass. Reference electrode 309 and either electrode 311 or 3 12 may be used for potentiometric detection. Sensor electrodes 311 and 312, both in the reaction zone, are used for conductivity detection. The electrodes should be made of platinum or other stable metals.

FIG. 2 is a potentiometric detector composed of Pyrex glass, platinum electrodes, and other metal electrodes, for the detection of electrolytes such as sulfite, bromine, chloride, and other reactable chemicals in a gas stream 1 entering through capillary 2. Gravity causes the solvent fluid 3, which is water or other solvents such as alcohols, to flow through tube 4 with an i.d. of 1 to 0.1 mm depending on the flow rate desired. Tube 4 has a length of 5 to 10 cm. The diameter of capillary 2, where it enters the contact zone, capillary 5, is from 1 to 0.01 mm in diameter and the diameter of capillary 5 is from 2 to 0.1 min. The gas stream entering capillary 5 through capillary 2 makes contact with the solvent fluid, and the gaseous compounds, which are potential electrolytes in the gas stream, enter the solvent fluid 3 in the contact zone. Fluids 1 and 3 both flow through the detector zone 6 which has electrodes 7 and 8 inside the 2 to 0.2 mm diameter i.d. capillary 5. The flow continues up through capillary 9 into the solution holder 10. The gas phase bubbles 11 escape out the top of holder 10. The cell has five other electrodes. Electrode 12 is a reference electrode, such as a silver/silver halide electrode. Electrodes 13, 14, 15 and 16 are two generator electrodes, a sensor electrode, and a reference electrode, respectively, for coulometric maintenance of constant concentration of a reactive chemical, such as bromine, in the bulk electrolyte solution in holder 10.

When sulfur dioxide, or any other reducing agent, enters the contact zone 5 in the gas stream, the oxidant (bromine) is decreased and the potential difference between electrodes 12 and 7 or 8 changes. This potential difference is recorded to detect and measure the amount of reactant in the gas stream. Other oxidants, such as iodine, may be used in place of bromine. Reactions such as complexation or precipitation may be used instead of redox reactions in this system. For example, silver ions may be used to precipitate chloride or other halides in the contact zone.

Figure 3:
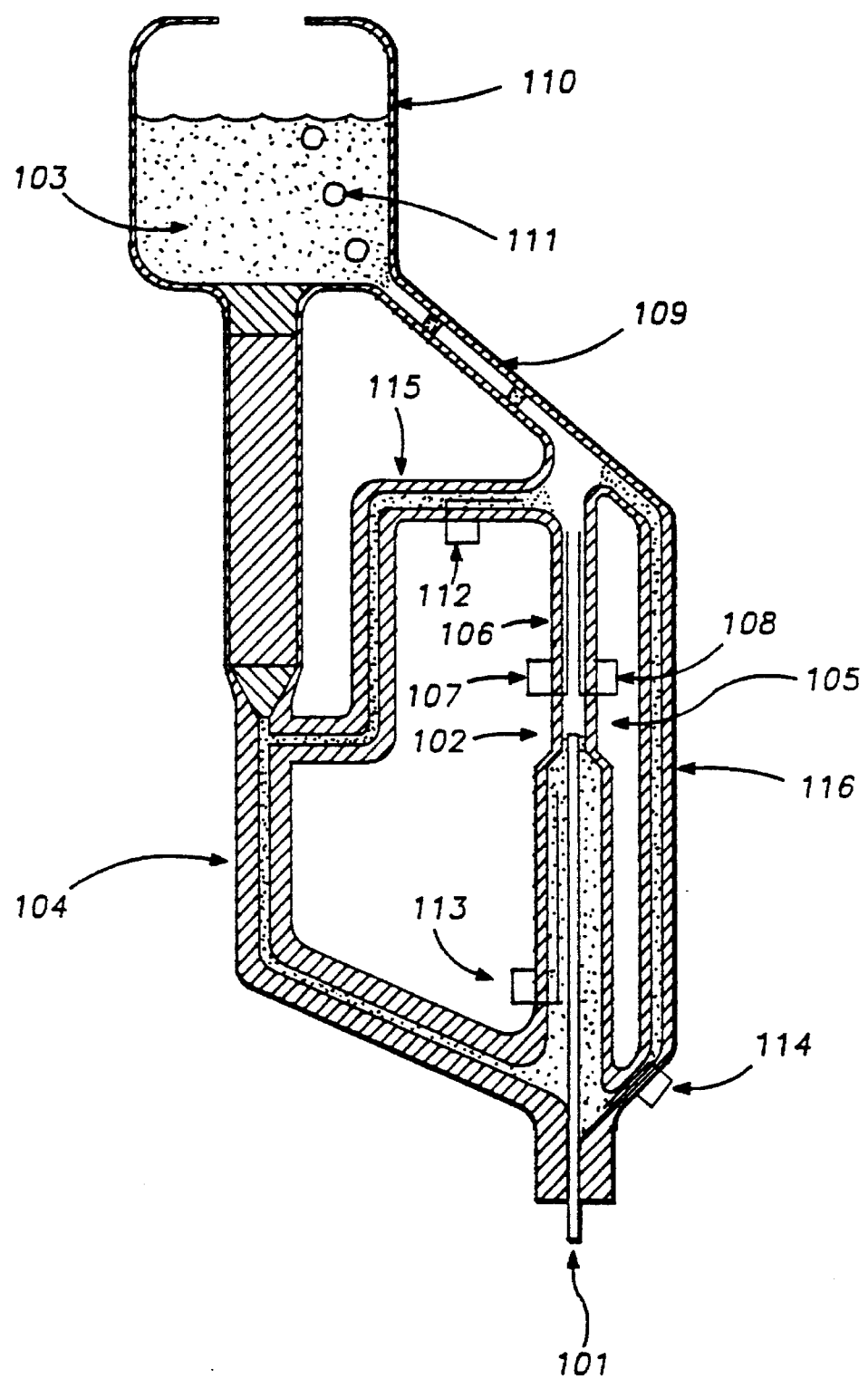
FIG. 3 is a cross section view of a coulometric detector incorporating gravimetric solvent feed.

FIG. 3 is a coulometric detector composed of Pyrex glass, platinum electrodes, and other metal electrodes, for the detection of electrolytes such as sulfite, bromine, chloride, and other reactable chemicals in a gas stream 101 entering through capillary 102. Gravity causes the solvent fluid 103, which is water and electrolytes or other solvents such as acetic acid, to flow through tube 104 with an i.d. of 1 to 0.1 mm depending on the flow rate desired. Tube 104 has a length of 5 to 10 cm. The diameter of capillary 102, where it enters the contact zone, capillary 105, is from 1 to 0.01 mm in diameter and the diameter of capillary 105 is from 2 to 0.1 min. The gas stream entering capillary 105 through capillary 102 makes contact with the solvent fluid and the gaseous compounds,, which are potential electrolytes in the gas stream, enter the solvent fluid 103 in the contact zone. Fluids 101 and 103 both flow upward through the detector zone 106 which has electrodes 107 and 108 inside the 2 to 0.2 mm diameter i.d. capillary 105. The flow continues up through capillary 109 into the solution holder 110. The gas phase bubbles 111 escape out the top of holder 110. Electrode 112 is a reference electrode, such as a silver/silver halide electrode. The electrolytic solution flows upward through capillaries 115 and 116. Electrodes 113 and 114 are two generator electrodes. The rate of generation is controlled by the sensor electrode 107 and/or 108 and reference electrode 112 for coulometric maintenance of a constant concentration of a reactive chemical, such as bromine, in the electrolyte solution in capillary 105.

When sulfur dioxide, or other reducing agent, enters the contact zone 106 in the gas stream, the oxidant (bromine) is decreased and the potential difference between electrodes 112 and 107 and/or 108 changes. This potential difference results in an increase in the generation rate of the titrant, which is recorded to detect and measure the amount of reactant in the gas stream. Other oxidants, such as iodine, may be used in place of bromine. Reactions such as complexation or precipitation may be used instead of redox reactions in this system. For example, silver ions may be used to precipitate chloride or other halides in the contact zone.

Figure 4:
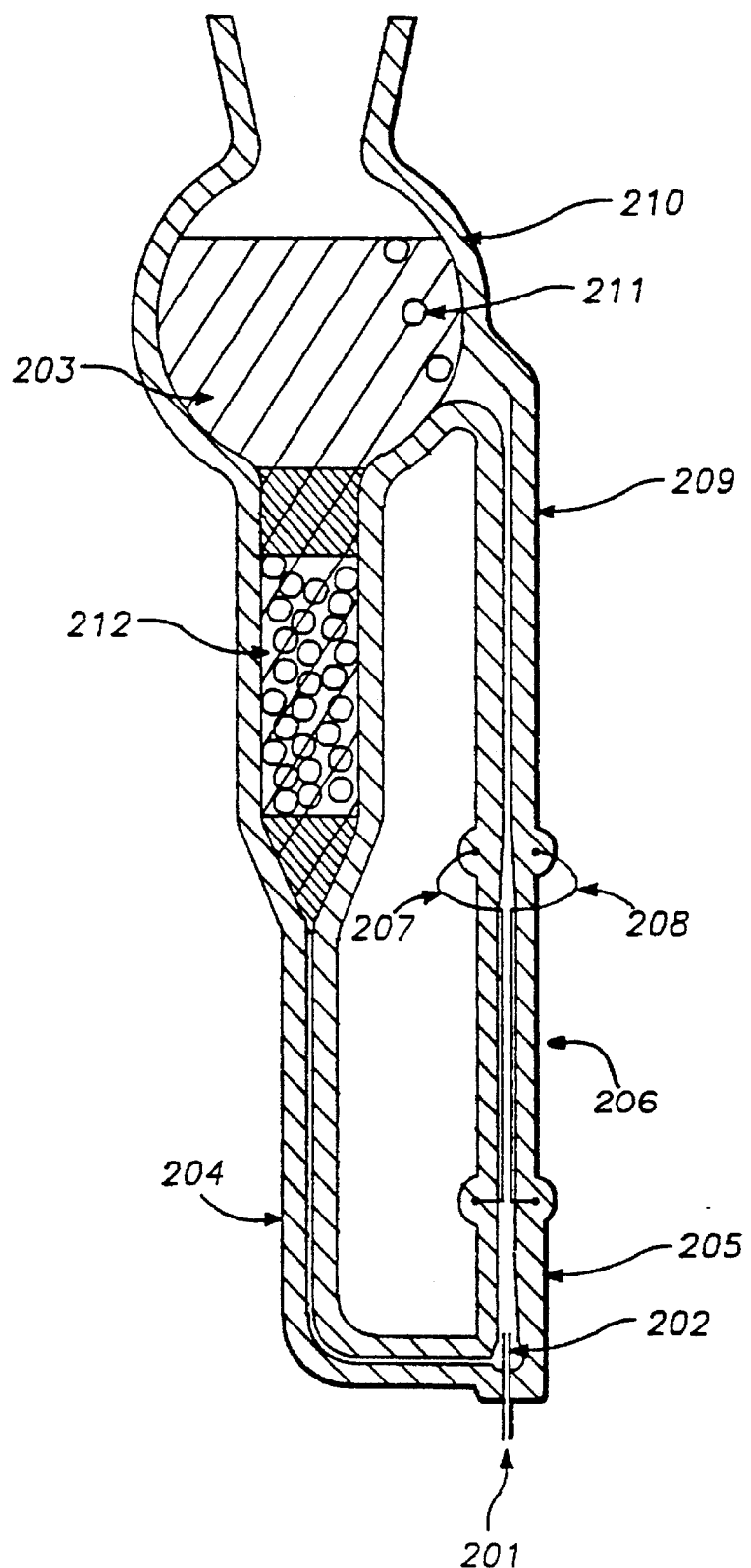
FIG. 4 is a cross section view of an electrolytic conductivity detector incorporating gravimetric solvent feed.

FIG. 4 is a conductimetric detector composed of Pyrex glass, platinum electrodes, and other metal electrodes for the detection of electrolytes such as hydrogen chloride, sulfur dioxide and other chemicals in a gas stream 201 entering through capillary 202. Gravity causes the solvent fluid 203, which is water or other solvents such as alcohols, to flow through the deionizer 212 and tube 204 with an i.d. of 1 to 0.1 mm depending on the flow rate desired. Tube 204 has a length of 5 to 10 cm. The diameter of capillary 202, where it enters the contact zone, capillary 205, is from 1 to 0.01 mm in diameter and the diameter of capillary 205 is from 2 to 0.1 min. The gas stream entering capillary 205 through capillary 202 makes contact with the solvent fluid and the gaseous compounds, which are potential electrolytes in the gas stream, enter the solvent fluid 203 in the contact zone. Fluids 201 and 203 both flow through the detector zone 206, which has electrodes 207 and 208 inside the 2 to 0.2 mm diameter i.d. capillary 205. The flow continues up through capillary 209 into the solution holder 210. The gas phase bubbles 211 escape out the holder 210. Electrolytic conductivity between electrodes 207 and 208 is measured and recorded as a function of time.

Figure 5:
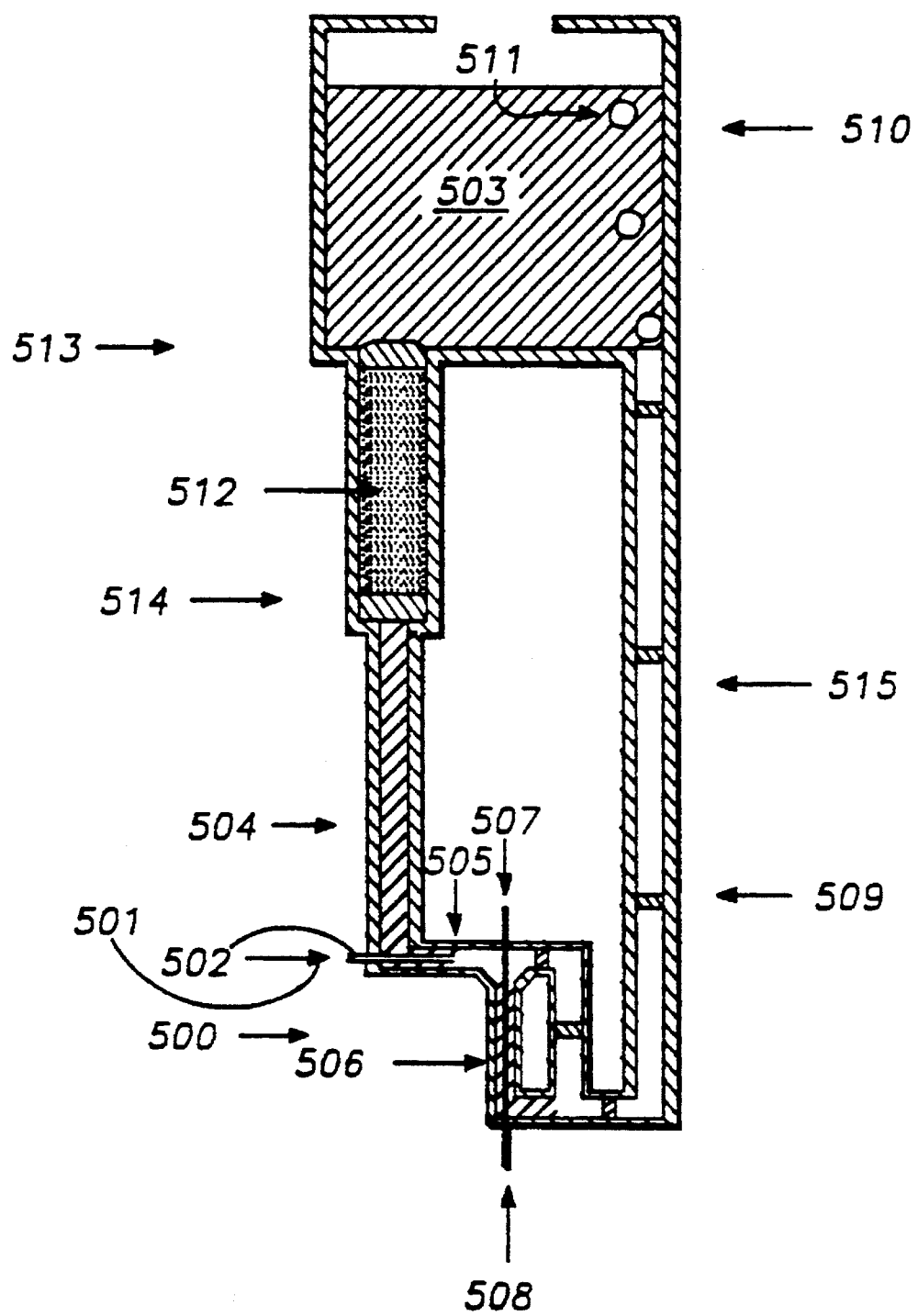
FIG. 5 is a cross section view of a gas-liquid separator conductimetric detector incorporating gravimetric solvent feed.

FIG. 5 is an electrical conductimetric detector similar to the detector of FIG. 4, but with a gas-liquid separator. Gas stream 501 enters through capillary 502 and contacts the liquid 503 flowing gravimetrically through deionizer 512 and flow controller capillary 504 to contact zone 505. The screens 513 and 514 hold the deionizer particles in place. Capillary 506, the detector zone with electrodes 507 and 508 near the gas-liquid separation point at the top of capillary 506, has liquid flow only. A small portion of the liquid and all of the gas pass capillary 506 to capillary 515. All of the liquid, as droplets 509, and all of the gas flow up capillary 515, entering the liquid reservoir 510. The gas bubbles 511 escape out the top and the liquid recycles. In its preferred form, the detector of FIG. 5 has a height of about 6.5 inches.

Figure 6:
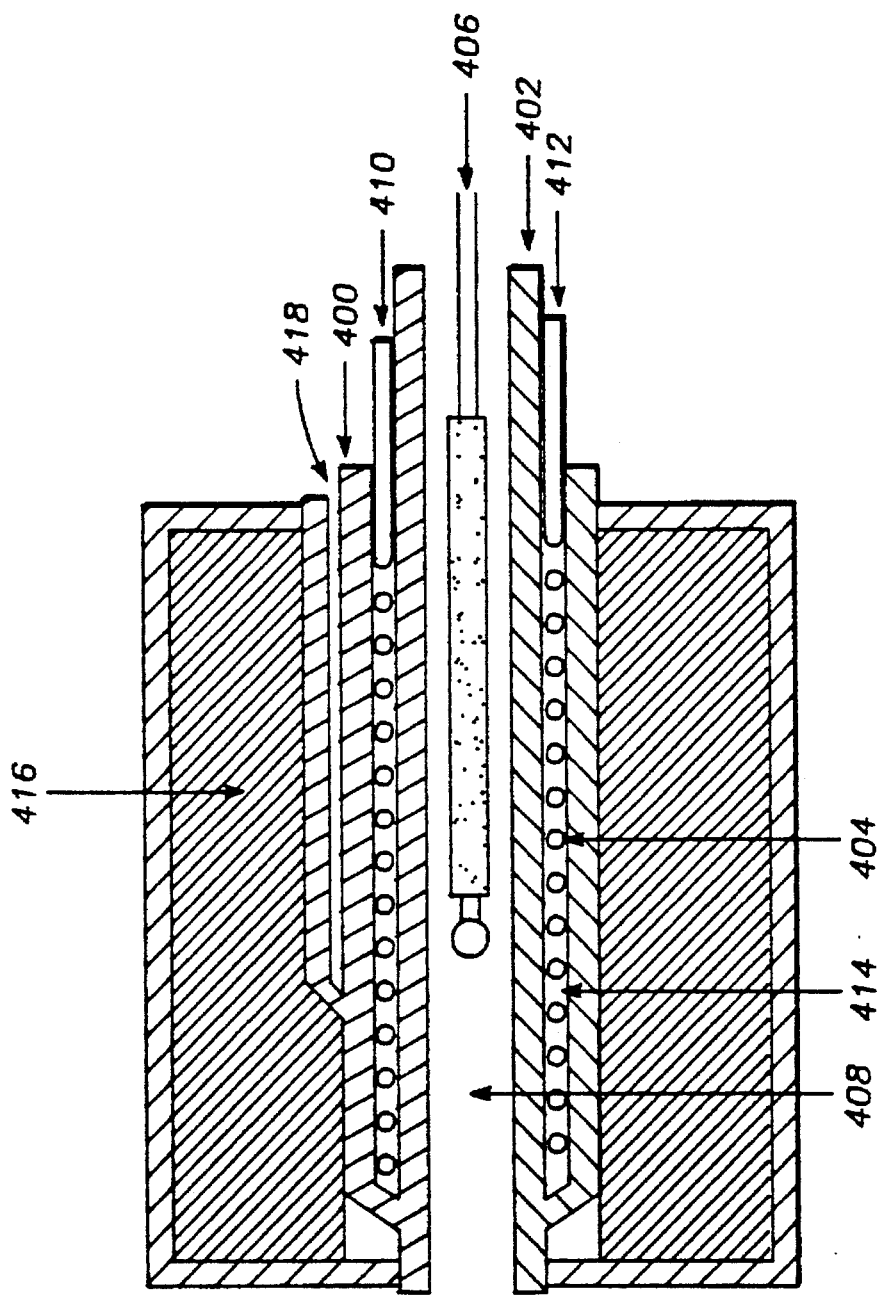
FIG. 6 is a cross section view of a pyrolysis furnace for use with the electrochemical detectors of FIGS. 1–5.

The gas stream entering any of the detectors shown in FIGS. 1–5 may be treated in a pyrolysis furnace as shown in FIG. 6 to convert organic compounds to potential electrolytes for detection. A special miniature furnace, that has a temperature controlled to within one degree centigrade at temperatures up to 1100 deg. centigrade, composed of first and second fused quartz electrically insulating tubes 400 and 402, a platinum heater coil 404, with a platinum-rhodium thermocouple 406 inside the pyrolysis furnace has very little field effect in pyrolysis zone 408 if the first end 410 of the heating coil 404 is wound from fight to left and back again to the second end 412. The heating coil 404 is wound for a length of approximately twelve centimeters on the outside of a 9 mm o.d. by 7 mm i.d. fused quartz electrically insulating tube 402, that has the thermocouple 406 inside and a 13 mm o.d. by 11 mm i.d. fused quartz electrically insulating tube 400 outside the heater coil. Fused quartz powder 414 is used to keep the platinum heater coil 404 from becoming shorted by filling the space between the two quartz tubes 400 and 402 with the powder 414. Alumina tubes may be used instead of fused quartz if higher temperatures are needed. Thermal insulation 416 is placed outside of the 13 mm o.d. tube 400. For less accurate temperature control, the thermocouple may be placed in a tube outside of the heating coil, such as tube 418. Presently available furnaces usually use an outside thermocouple location.

Figure 7:
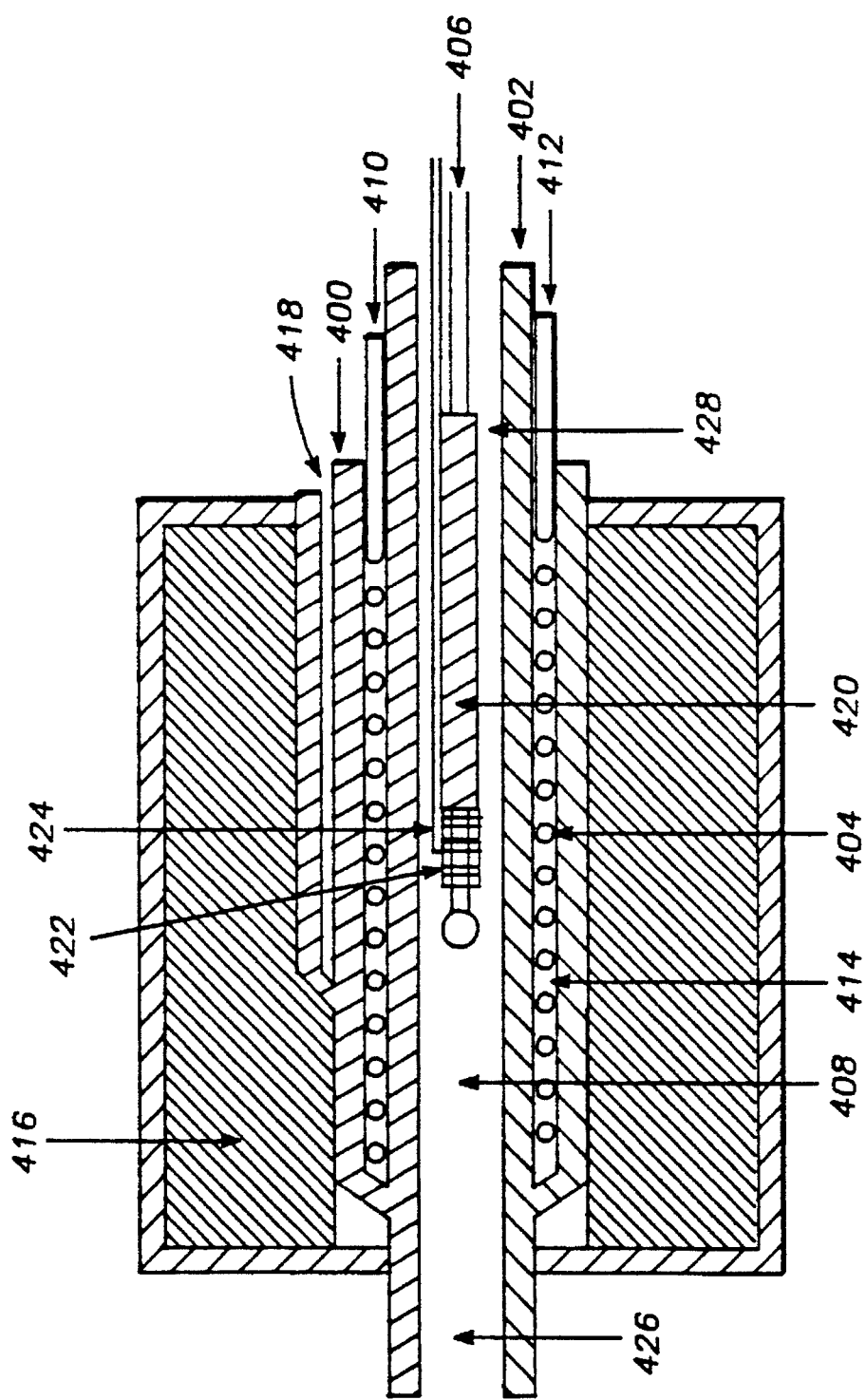
FIG. 7 is a cross section view similar to FIG. 6, but of another embodiment of a pyrolysis furnace modified for use as a gas phase electrolytic conductivity detector.

The furnace in FIG. 6 may also be used as a gas phase electrolytic conductivity detector (GPELCD) simply by inserting an anode and a cathode. As shown in FIG. 7, normally thermocouple 406 may be used as the cathode. The cathode is introduced through a quartz tube 420 and a catalyst material 422, such as mullite or alumina. The anode 424, which is a platinum wire, is wound on the catalyst 422. The gas inlet is placed at the left end of FIG. 7 at position 426, and the gas outlet is at position 428. The normal gas composition that comes out of a FID on a gas chromatograph may be introduced into the detector of FIG. 7 at position 426, with or without changing the gas phase composition.

Figure 8:
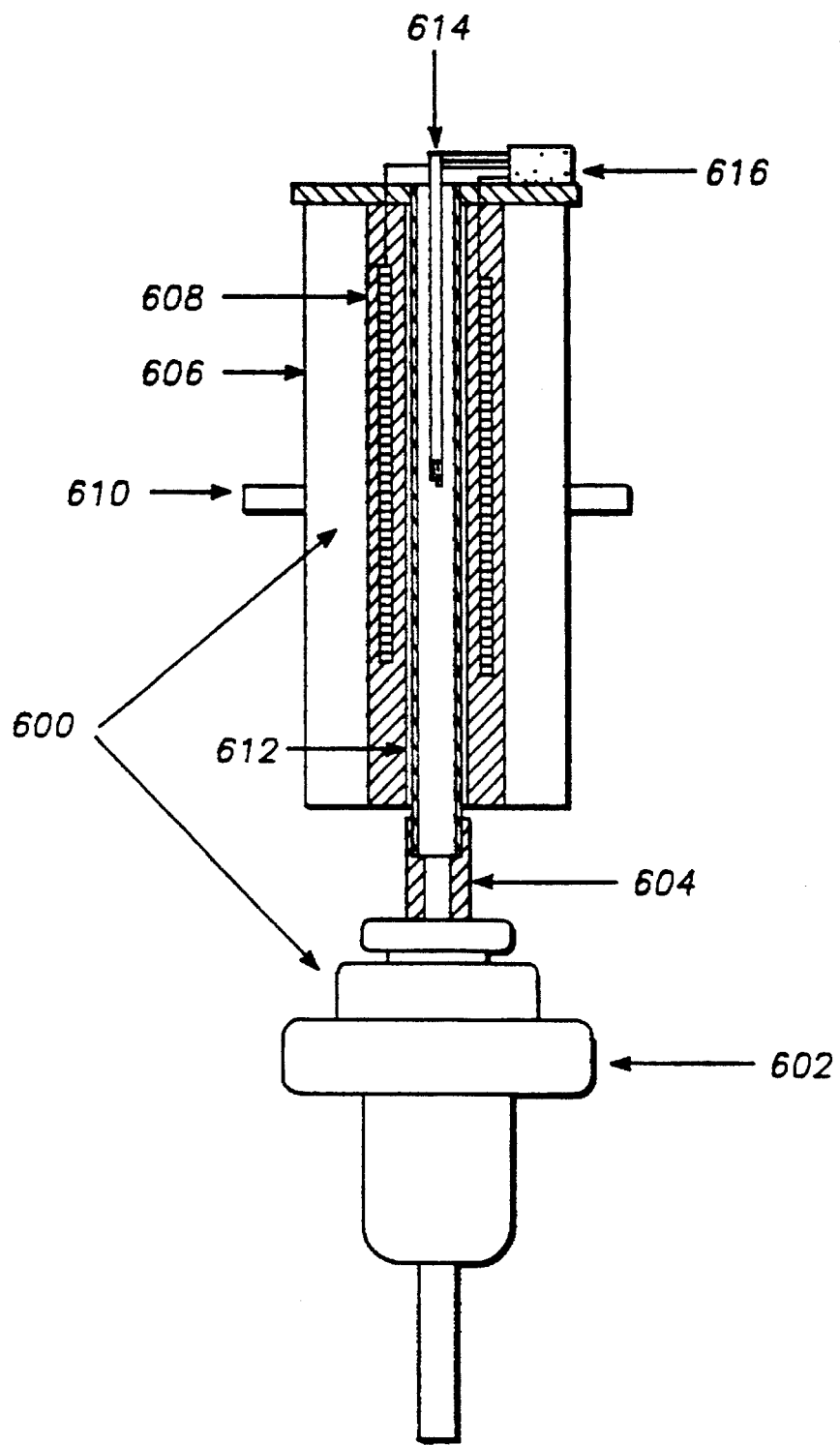
FIG. 8 is a cross section view of a gas phase electrolytic conductivity detector similar to FIG. 7 in combination with a flame ionization detector.

FIG. 8 shows a combination of a GPELCD and a FID, taking the regular output gas from the FID directly into the GPELCD without modification. In the combination 600 of FIG. 8, the FID 602 is leak sealed at 604 to the input of fused quartz or alumina tube 612 in the GPELCD furnace 606. The furnace 606 has a special heating coil 608 that gives very little electrical field effect inside the tube 612. Thermocouple and metal electrodes are used as the temperature controller and gas phase current electrodes in detector circuits 614 connected to 6-wire output connector 616. The wires of connector 616 are insulated in fused quartz. A catalyst of alumina or mullite is provided at the center of the furnace 606, which is controlled to 1° C. in the temperature range of 700° to 1100° C. Mounting supports 610 are provided on either side of the GPELCD furnace 606. Alternatively, the FID 602 could be replaced by a photoionization detector or by the direct output of a gas chromatograph.

Figure 9A:
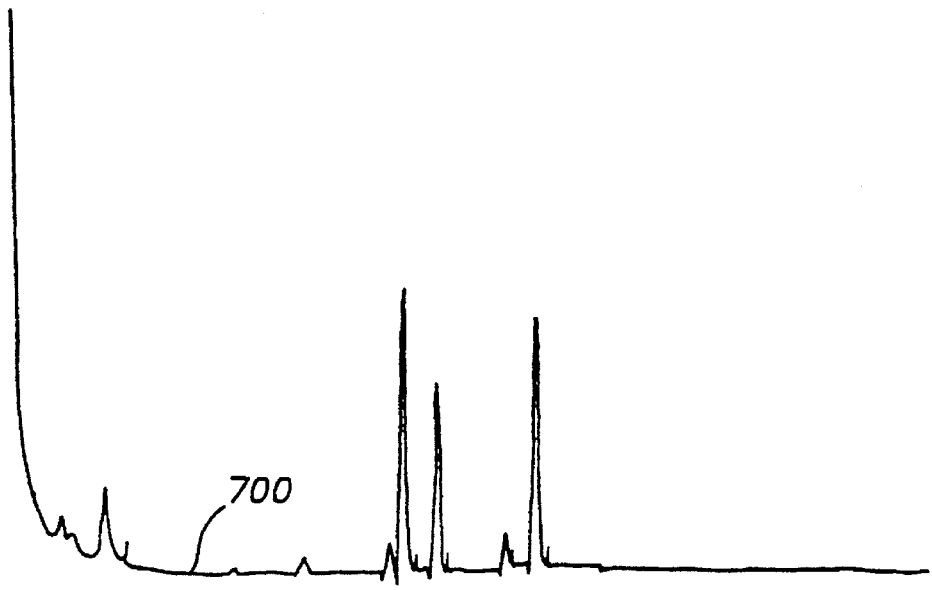
Figure 9B:

FIGS. 9A and 9B show experimental data for the combination of the FID 602 and the GPELCD 606 in FIG. 8. Curves 700 and 702 are for standards containing compounds with and without chlorine present. The ten peaks 1–10 in the curves 700 and 702, with some of the peaks present in both curves, are the solvent (methanol), methylene chloride, acetone, chloroform, methylchloroform, trichloroethylene, benzene, hexane, tetrachloroethylene and toluene, respectively. The chlorinated compounds gave very small peaks in the FID 602. On the other hand, the GPELCD 606 gave no peaks at all for the non-chlorine containing compounds. The mounts of the compounds in these curves are in the nanogram range, except for the methanol solvent, which gave no peak at all in the GPELCD.

The results of three standard runs and one air sample are shown in FIGS. 10A–10D, using a combination of FID 602 and GPELCD 606 in FIG. 8. The seven peaks in curves 800, 802 and 804 (FIGS. 10A–10C) are, from left to right, methylene chloride at 806A–806C, chloroform at 808A–808C, freon at 810A–810C, carbon tetrachloride at 812A–812C, trichloroethylene at 814A–814C, tetrachloroethylene at 816A–816C and chlorobenzene at 818A–818C. The GPELCD 606 gave no peaks at all for methanol, acetone, benzene, hexane and toluene, the non-chlorine containing compounds that were present in curves 800, 802 and 804, which were 0.5, 1 and 2 microliters, respectively, of the standard solution in methanol. The amounts of the compounds in-these curves are in the nanogram range, except for the solvent that entered the detector in one to three minutes and gave no peak at all in the GPELCD 606. The curves 800, 802 and 804 show that the response of the GPELCD 606 is linear for these compounds. Curve 820 represents 174 liters of outdoor air in Menlo Park, Calif. on the night of Oct. 7–8, 1992, collected on a special thermal-desorbable charcoal tube. It contained additional chloro-compounds, such as methyl chloroform at peak 822, freon 11 at peak 824, and several others not yet identified. The levels are in the 10 to 500 pans per trillion, on a gas volume basis.

The gravity electrolyte flow controlled electrochemical potentiometric, coulometric, and conductimetric detectors use flow rates approximately, but not limited to, 2 to 0.1 ml per minute with gas flow rates in the range of 10 to 1000 ml per minute. All three types of detectors have sensitivities of picograms per second for elements such as sulfur and halogens.

It should further be apparent to those skilled in the an that various changes in form and details of the invention as shown and described may be made. It is intended that such changes be included within the spirit and scope of the claims appended hereto.

What is claimed is:

1. An electrochemical detection cell, which comprises a gravimetric electrolyte input flow capillary tube intersecting a second capillary tube at a given point, a gas stream input flow capillary tube for a gas containing a substance to be detected, said gas stream input flow capillary tube entering said second capillary tube proximate to the given point, said second capillary tube forming a mixing zone at the given point, at least one sensor electrode positioned in said second capillary tube spaced from and beyond the given point, and an electrolyte reservoir connected to said gravimetric electrolyte input flow capillary tube and positioned above said gravimetric electrolyte input flow capillary tube, said second capillary tube having an exit for the electrolyte and the gas stream beyond said at least one sensor electrode, the exit of said second capillary tube being connected to said electrolyte reservoir.

2. The electrochemical detection cell of claim 1 additionally comprising a reference electrode in said gravimetric electrolyte input flow capillary tube.

3. The electrochemical detection cell of claim 1 in which said at least one sensor electrode comprises a pair of sensor electrodes.

4. The electrochemical detection cell of claim 1 in which said gas stream input flow capillary tube is formed from a non-wettable plastic.

5. The electrochemical detection cell of claim 2 in which said reference electrode is a silver/silver halide electrode.

6. The electrochemical detection cell of claim 2 in which said at least one sensor electrode comprises a pair of sensor electrodes.

7. The electrochemical detection cell of claim 6 additionally comprising a pair of generator electrodes, an additional sensor electrode and an additional reference electrode in said electrolyte reservoir.

8. The electrochemical detection cell of claim 1 additionally comprising a reference capillary tube connected between said gravimetric electrolyte input flow capillary tube and said second capillary tube above said at least one sensor electrode, and a reference electrode in said reference capillary tube.

9. The electrochemical detection cell of claim 8 additionally comprising a bypass capillary tube connected between said gravimetric electrolyte input flow capillary tube and said second capillary tube above said at least one sensor electrode, a first generator electrode in said gravimetric electrolyte input flow capillary tube, and a second generator electrode in said bypass capillary tube.

10. The electrochemical detection cell of claim 9 in which said at least one sensor electrode comprises a pair of sensor electrodes.

11. In combination, the electrochemical detection cell of claim 1 and a pyrolysis furnace connected to said gas stream input flow capillary tube to provide the gas.

12. The combination of claim 11 in which said pyrolysis furnace comprises first and second concentrically positioned electrically insulating tubes, and a resistance heater wound around said first electrically insulating tube between said first electrically insulating tube and said second electrically insulating tube.

13. The combination of claim 12 in which said heating coil is wound from a first end of said first electrically insulating tube to a second end of said first electrically insulating tube and back again to the first end, said pyrolysis furnace additionally comprising fused electrically insulating powder between said first and second electrically insulating tubes to prevent shorting of said heating coil.

14. An electrochemical detection method which comprises supplying an electrolyte solution through a gravimetric electrolyte input flow capillary tube from an electrolyte reservoir positioned above said capillary tube to a mixing zone at a flow rate controlled by the capillary tube, supplying a gas containing a detectable substance through a gas input capillary tube to the mixing zone, mixing the electrolyte solution and the gas in the mixing zone, passing the electrolyte solution and gas from the mixing zone to a detection zone, detecting the detectable substance in the electrolyte solution within the detection zone, and flowing the electrolyte solution and gas from the detection zone into the reservoir.

15. The electrochemical detection method of claim 14 in which the detectable substance is detected potentiometrically.

16. The electrochemical detection method of claim 14 in which the detectable substance detected coulometrically.

17. The electrochemical detection method of claim 14 in which the detectable substance is detected conductimetrically.

18. The electrochemical detection method of claim 14 in which the gas containing a detectable substance is supplied from a pyrolysis furnace.

19. An electrochemical detection method which comprises supplying an electrolyte solution through a gravimetric electrolyte input flow capillary tube from an electrolyte reservoir to a mixing zone at a flow rate controlled by the capillary tube, supplying a gas containing a detectable substance through a gas input capillary tube to the mixing zone, mixing the electrolyte solution and the gas in the mixing zone, passing the electrolyte solution and gas from the mixing zone to a detection zone, detecting the detectable substance in the electrolyte solution within the detection zone, and flowing the electrolyte solution and the gas from the detection zone into the reservoir.

20. The electrochemical detection method of claim 19 in which the electrolyte solution and gas are separated in a gas-liquid separator containing sensor electrodes after the mixing zone and before the gas and the electrolyte solution are flowed into the reservoir.

21. A pyrolysis furnace for use in an electrochemical detection cell which comprises first and second concentrically positioned electrically insulating tubes, and a resistance heating coil wound in a first direction from a first end of said first electrically insulating tube to a second end of said first electrically insulating tube and back again in the first direction to the first end, said heating coil mounted between said first electrically insulating tube and said second electrically insulating tube.

22. The pyrolysis furnace of claim 21 in which said pyrolysis furnace additionally comprises fused electrically insulating powder between said first and second electrically insulating tubes to prevent shorting of said heating coil.

23. The pyrolysis furnace of claim 22 additionally comprising a thermocouple in said first electrically insulating tube.

24. The pyrolysis furnace of claim 23 in which said pyrolysis furnace comprises a gas phase electrolytic conductivity detector, said thermocouple comprises a cathode of said gas phase electrolytic conductivity detector, and said pyrolysis furnace additionally comprises an anode of said gas phase electrolytic conductivity detector.

25. The pyrolysis furnace of claim 23 additionally comprising a layer of thermally insulating material on said second electrically insulating tube.

26. The pyrolysis furnace of claim 24 in combination with a source of a chlorine containing sample connected to said second electrically insulating tube and a source of a gas for reacting with the chlorine containing sample to produce ionizable chlorine.

27. The pyrolysis furnace of claim 24 in combination with a source of a sample containing an ionizable element other than carbon, nitrogen and hydrogen connected to said second electrically insulating tube.

28. The combination of claim 27 in which said source of a sample containing an ionizable element comprises a flame ionization detector, a photoionization detector or a direct output of a gas chromatograph.

29. The combination of claim 28 in which the flame ionization detector, photoionization detector or direct output of a gas chromatograph is a source of a sample containing chlorine, bromine, sulfur, nitrogen or phosphorus.

30. The pyrolysis furnace of claim 28 in which said source of a sample containing an ionizable element comprises a gas chromatograph.

31. The combination of claim 26 in which said source of the gas is an oxygen, hydrogen or mixture of oxygen and hydrogen source.

32. The combination of claim 26 in which said source of a chlorine containing sample comprises a flame ionization detector, a photoionization detector or a direct output of a gas chromatograph.

* * * * *